United States Patent
Dubke et al.

(10) Patent No.: US 9,513,200 B1
(45) Date of Patent: Dec. 6, 2016

(54) DETERMINATION OF A THRESHOLD CRACK LENGTH

(71) Applicant: Rolls-Royce Corporation, Indianapolis, IN (US)

(72) Inventors: Jonathan Dubke, Avon, IN (US); Paul Brett Wheelock, Carmel, IN (US)

(73) Assignee: ROLLS-ROYCE CORPORATION, Indianapolis, IN (US)

(*) Notice: Subject to any disclaimer, the term of this patent is extended or adjusted under 35 U.S.C. 154(b) by 0 days.

(21) Appl. No.: 14/932,659

(22) Filed: Nov. 4, 2015

(51) Int. Cl.
*G01N 3/20* (2006.01)

(52) U.S. Cl.
CPC ...................................... *G01N 3/20* (2013.01)

(58) Field of Classification Search
CPC ............. C03C 23/0025; C03C 17/322; G01N 2203/0066; G01N 3/32
USPC .......................................................... 73/799
See application file for complete search history.

(56) References Cited

U.S. PATENT DOCUMENTS

| | | | |
|---|---|---|---|
| 4,916,954 A * | 4/1990 | Buzzard | G01N 3/08 73/799 |
| 4,924,708 A * | 5/1990 | Solomon | G01N 3/08 73/799 |
| 6,532,825 B1 * | 3/2003 | Abe | G01M 5/0033 73/799 |
| 7,219,044 B1 | 5/2007 | Prevey et al. | |
| 7,889,840 B2 | 2/2011 | Vasudevan et al. | |
| 8,209,839 B1 | 7/2012 | Brostmeyer et al. | |
| 8,291,589 B2 | 10/2012 | Davis et al. | |
| 8,505,181 B1 | 8/2013 | Brostmeyer et al. | |
| 8,544,338 B2 * | 10/2013 | Pettit | G01N 3/38 73/808 |
| 8,549,929 B2 * | 10/2013 | Seok | G01N 3/04 73/851 |
| 8,712,739 B2 | 4/2014 | Jiang et al. | |
| 8,984,955 B2 * | 3/2015 | Mouri | B23P 6/04 73/788 |
| 9,151,706 B2 * | 10/2015 | Wada | G01N 17/00 |
| 2008/0243457 A1 | 10/2008 | deLaneuville | |
| 2010/0153080 A1 | 6/2010 | Khan et al. | |
| 2014/0207419 A1 | 7/2014 | Messinger et al. | |
| 2014/0229149 A1 | 8/2014 | Guan et al. | |
| 2015/0219539 A1 * | 8/2015 | Mary | G01N 29/043 73/799 |

(Continued)

OTHER PUBLICATIONS

He, et al., "Asymmetric Four-Point Crack Specimen," Journal of Applied Mechanics, vol. 67, Mar. 2000, pp. 207-209.

(Continued)

*Primary Examiner* — Lisa Caputo
*Assistant Examiner* — Octavia Hollington
(74) *Attorney, Agent, or Firm* — Shumaker & Sieffert, P.A.

(57) ABSTRACT

A method for determining a threshold crack length in a machine component including a fatigue crack defining a fatigue crack length and a fatigue crack angle. The method includes determining a component threshold stress intensity factor for the fatigue crack angle, determined from a dataset that includes threshold stress intensity factors for mixed-mode phase angles formed by conducting an asymmetric four point bend test on a test specimen having an initial notch. The method includes determining a threshold crack length based on the component fatigue crack length and fatigue crack angle using a formula disclosed herein.

14 Claims, 6 Drawing Sheets

(56) References Cited

U.S. PATENT DOCUMENTS

2015/0274587 A1* 10/2015 Barthelat ................ C03B 33/04
29/428

OTHER PUBLICATIONS

Campbell, et al., "Mixed-mode, high-cycle fatigue-crack growth thresholds in Ti-6A1-4V I. A Comparison of large and short-crack behavior," Engineering Fracture Mechanics, revised May 4, 2000, vol. 67, pp. 209-227.
Haddad, et al., "Fatigue Crack Propagation of Short Cracks," Transactions of the ASME, vol. 101, Jan. 1979, pp. 42-46.
Nalla, et al., "Effects of microstructure on mixed-mode, high-cycle fatigue crack-growth thresholds in Ti-6A1-4V alloy," Fatigue Fract Engng Mater Struct, vol. 25, Jan. 10, 2002, pp. 587-606.
Nalla, et al., "Mixed-mode, high-cycle fatigue-crack growth thresholds in Ti-6A1-4V: Role of small cracks," International Journal of Fatigue, vol. 24, Jan. 25, 2002, pp. 1047-1062.

* cited by examiner

DETERMINATION OF A THRESHOLD CRACK LENGTH

TECHNICAL FIELD

The disclosure describes techniques for determining whether a flaw in an article exceeds a threshold size.

BACKGROUND

Machine components may undergo a variety of mixed mode loading forces during routine operation. The variety of mixed mode loading forces may cause small flaws in the machine component that initiate fatigue cracks which propagate with time leading to premature impairment of the component, shortened lifespan of the component, or both.

SUMMARY

The disclosure describes various techniques for determining whether a fatigue crack in a machine component exceeds a threshold limit that could cause the fatigue crack to grow during routine operation leading to premature impairment or failure of the component. The fatigue crack may be present in the machine component at a particular length and a particular angle with respect to the principal stress from the applied loads.

In some examples, the present disclosure describes a method that includes determining a fatigue crack length and a fatigue crack angle of a fatigue crack of a machine component, where the fatigue crack angle is measured as an angle between a normal to a plane defined by the fatigue crack and a direction of the anticipated cyclic load force to be applied to the machine component. The method may also include determining a component threshold stress intensity factor for the fatigue crack, where the component threshold stress intensity factor is determined from a dataset formed by at least conducting an asymmetric four point bend test on a test specimen having an initial notch, where the dataset includes at least one respective threshold stress intensity factor and at least one mixed-mode phase angle, where each respective threshold stress intensity factor of the at least one respective threshold stress intensity factor is associated with a corresponding mixed-mode phase angle of the at least one mixed-mode phase angle, and where the component threshold stress intensity factor is based at least in part on a threshold stress intensity factor associated with a mixed-mode phase angle that corresponds to the fatigue crack angle. The method may also include determining a threshold crack length for the component threshold stress intensity factor based on Equation 1. The method may also include categorizing a condition of the machine component based at least in part on a comparison between the threshold crack length and the fatigue crack length of the fatigue crack in the machine component.

In another example, the disclosure describes a method that includes determining a fatigue crack length and a fatigue crack angle of a fatigue crack of a machine component, where the fatigue crack angle is measured as an angle between a normal to a plane defined by the fatigue crack and a direction of the anticipated cyclic load force to be applied to the machine component. The method may include conducting an asymmetric four point bend test at a mixed-mode phase angle on a test specimen having an initial notch to determine a threshold stress intensity factor that results in a growth of a crack from the initial notch, where the mixed-mode phase angle is set to equal the fatigue crack angle of the machine component, where the test specimen has a composition substantially similar to the machine component. The method may include determining a threshold crack length for the threshold stress intensity factor based on Equation 1. The method may include comparing the threshold crack length to the fatigue crack length of the fatigue crack of the machine component. The method may include categorizing a condition of the machine component based on comparing the threshold crack length to the fatigue crack length of the fatigue crack in the machine component.

In another example, the disclosure describes a device that includes a processor configured to analyze a dataset to determine a component threshold stress intensity factor for a machine component, where the machine component includes a fatigue crack having a fatigue crack length and a fatigue crack angle measured as an angle between a normal to a plane defined by the fatigue crack and a direction of the anticipated cyclic load force to be applied to the machine component, where the dataset is formed by at least conducting an asymmetric four point bend test on a test specimen having an initial notch, where the dataset includes at least one respective threshold stress intensity factor and at least one mixed-mode phase angle, where each respective threshold stress intensity factor of the at least one respective threshold stress intensity factor is associated with a corresponding mixed-mode phase angle of the at least one mixed-mode phase angle, and where the component threshold stress intensity factor is based at least in part on a threshold stress intensity factor associated with a mixed-mode phase angle that corresponds to the fatigue crack angle, where the processor is configured to determine a threshold crack length for the machine component using the component threshold stress intensity factor based on Equation 1, and where the processor is configured to compare the threshold crack length and the fatigue crack length and categorize a condition of the machine component based at least in part on the comparison.

The details of one or more examples are set forth in the accompanying drawings and the accompanying description below. Other features, objects, and advantages will be apparent from the description and drawings, and from the claims.

DETAILED DESCRIPTION

Figure 1:
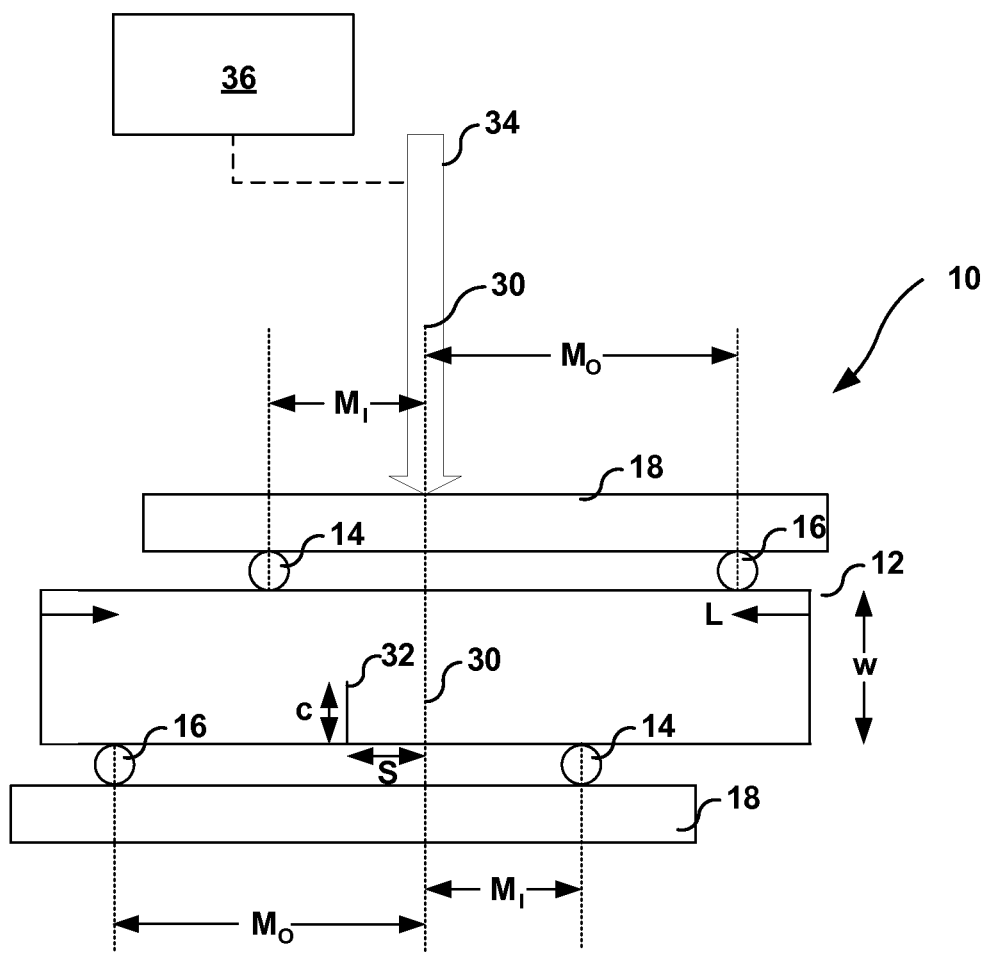
FIG. 1 is a conceptual side view of a standardized asymmetric four-point bending test.

The disclosure describes various techniques and a device for determining whether a screened flaw, e.g., fatigue crack, present in a machine component at a particular length and angle may exceed a threshold size that could cause the fatigue crack to propagate during routine operation and lead to premature impairment or failure of the component.

Flaws in machine components may occur in many aerospace and manufacturing applications. The flaws may occur in machine components due to one or more of a variety of causes including, for example, inclusions or other imperfections of the base materials used to make the component, consequences of the manufacturing process, e.g., machine or tool marks, damage to the component resulting from debris, or fatigue of the component resulting from routine operation. Eventually the flaws may produce a fatigue crack in the component that can grow with time as a result of routine operation (e.g., stress on the component). The growth of a fatigue crack may be dependent on a variety of factors including, for example, the composition, microstructure, and toughness of the machine component, as well as the initial length of the fatigue crack (e.g., flaw), the anticipated loads to be applied to the machine component, and the angle between the fatigue crack and the direction of the anticipated loads. In some cases, small fatigue cracks may be tolerated without significant reduction in the useful life of the machine component (e.g., a decrease in all or part of the intended life of the component). This may be due in part to the elasticity of the machine component and the ability of the component to withstand some cyclic loading without the flaw or fatigue crack undergoing any significant growth.

In some examples, the length of the fatigue crack initiating from a flaw (e.g., $a_o$) may reach a critical or threshold size (e.g., $a_{th}$) such that the anticipated loads applied to the machine component cause the fatigue crack to grow with time under the loads that occur during routine operation.

The present disclosure describes several techniques to determine whether a particular fatigue crack in a machine component meets or exceeds a threshold length that may lead to premature impairment or failure of the component caused by unwanted growth of the fatigue crack. In some examples, the described techniques may be used to categorize a condition of the machine component such as determining whether the machine component is below operational or quality control specifications and/or due for replacement.

In some examples, the threshold crack length (e.g., $a_{th}$) for a machine component may be determined by conducting cyclic load experiments on a test specimen having substantially the same composition (e.g., the same or nearly the same composition) as the machine component being evaluated. The test specimen includes an initial notch from which a simulated fatigue crack will initiate and propagate to simulate the growth and characteristic of a fatigue crack in the machine component. The results of the cyclic load experiments provide a threshold stress intensity factor (e.g., $\Delta K_{th}$) that indicates the point when the cyclic stresses on the test specimen cause the simulated fatigue crack to reach a critical size where further crack growth would be unstable, impairing the ability of the component to sustain operational loads. Equation 1 below provides an example equation for determining a predictive threshold crack length $a_{th}$ for a machine component based on the threshold stress intensity factor (e.g., $\Delta K_{th}$) obtained from the cyclic load experiments.

$$a_{th} = \frac{1}{\pi}\left[\frac{\Delta K_{th}}{\Delta \sigma \beta}\right]^2 - a' \qquad \text{(Equation 1)}$$

where $a_{th}$ represents the threshold crack length, a' represents a small-crack correction factor, $\Delta K_{th}$ represents the threshold stress intensity factor, $\Delta \Gamma$ represents the anticipated stress cycle to be applied to the machine component, and $\beta$ represents a geometry correction factor. The anticipated stress to be applied to the machine component, may be determined from finite element analysis or classical engineering stress equations.

The small-crack correction factor a', also known as an El-Haddad correction factor, may be determined empirically from fatigue crack growth testing on small cracks. Such testing is described in "Fatigue Crack Propagation of Short Cracks," by El Haddad et al., 42 Transactions of the ASME vol. 101, January 1979 at 42-46, the contents of which is hereby incorporated by reference in its entirety. In some examples, the small-crack correction factor a' may be assumed as zero.

The geometry correction factor $\beta$ may be determined from established solutions available in technical literature or through structural crack growth analysis. One literature source for determining geometry correction factor $\beta$ is "Compendium of Stress Intensity Factors," by Rooke and Cartwright, Procurement Executive, Ministry of Defense. H. M. S. O., 1976. In some examples, the geometry correction factor $\beta$ may be assumed as one.

The anticipated stress cycle Au corresponds to the anticipated cyclic load forces that are exerted on the actual machine component being analyzed. The anticipated stress cycle Au may be determined by classical engineering calculations or finite element analysis, which are understood by those in the art.

The threshold stress intensity factor $\Delta K_{th}$ may be determined experimentally. In some examples, the threshold stress intensity factor $\Delta K_{th}$ may be determined by conducting a plane-strain crack toughness test such as the standardized ASTM E-399 tests using test specimens of substantially the same composition (e.g., the same chemical composition or nearly the same chemical composition) as the machine component. The resultant threshold stress intensity factors $\Delta K_{th}$ derived from these experiments may then be used in Equation 1 to determine a threshold crack length $a_{th}$. ASTM E-399 tests determine the threshold stress intensity factors $\Delta K_{th}$ and threshold crack lengths $a_{th}$ by applying Mode I load forces to a simulated fatigue cracks in the test specimens to determine the critical point of propagation. During normal operation of the machine components however, the flaws or fatigue cracks in machine components may be subjected to mixed-mode load forces (e.g., including Mode I and Mode II load forces) due to the angle between the fatigue crack and the load forces applied to the machine component, rather than solely Mode I forces. As a result, the threshold crack length, $a_{th}$, calculated based on the standardized ASTM E-399 tests may be inaccurate, depending on the angle of the fatigue crack (e.g., "fatigue crack angle") in the machine component. The present disclosure provides a method of determining a predictive threshold crack length $a_{th}$ for the machine component based in part on a threshold stress intensity factor $\Delta K_{th}$ obtained from mixed-mode loading forces (e.g., Mode I and Mode II) that also accounts for the fatigue crack angle fatigue crack with respect to the loading forces.

Figure 4:
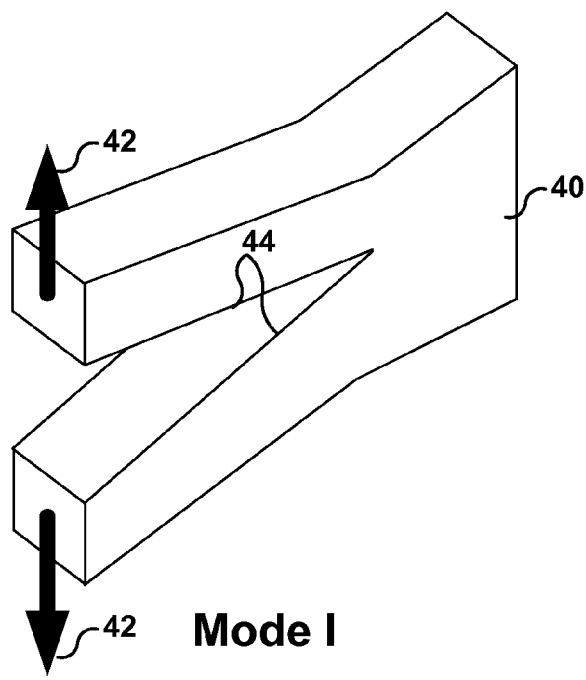
FIG. 4 is a conceptual perspective view of Mode I loading forces applied to a fatigue crack of a machine component.

As used herein, a normal mode load force, tensile loading, or a Mode I load force is used to describe stress forces that are applied substantially orthogonal (e.g., orthogonal or nearly orthogonal) and in opposite directions to a fatigue crack. Mode I load forces can be described as an opening force causing sides of a fatigue crack to be pulled in opposite directions of one another. FIG. 4 shows conceptual perspective view of Mode I load forces 42 applied to a fatigue crack 44 of a machine component 40 causing fatigue crack 44 to "open," resulting in propagation of fatigue crack 44.

Figure 5:
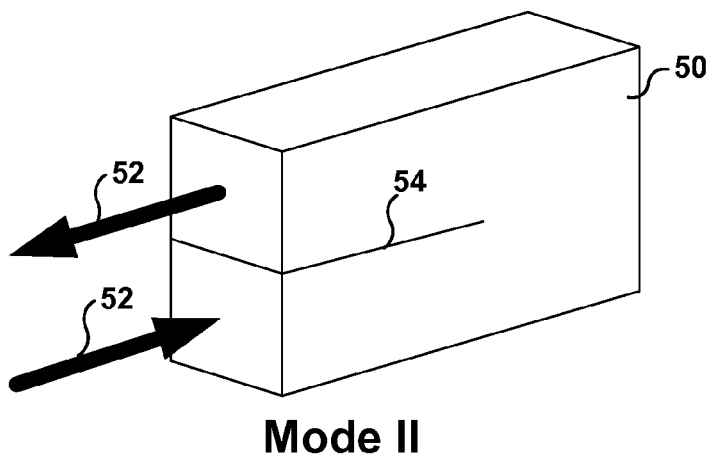
FIG. 5 is a conceptual perspective view of Mode II loading forces applied to a fatigue crack of a machine component.

As used herein, a sliding load force, shear, or Mode II load force is used to describe stress forces that are substantially parallel (e.g., parallel nearly parallel) to a fatigue crack. Mode II load forces can be described as an in-plane shearing forces causing the opposite sides of the fatigue crack to slide past one another in opposite directions towards and away from the crack edge. FIG. 5 shows conceptual perspective view of Mode II loading forces 52 applied to a fatigue crack 54 of a machine component 50, causing fatigue crack 54 to undergo in-plane shearing forces along fatigue crack 54 (e.g., "sliding"), resulting in crack propagation.

The threshold stress intensity factors $\Delta K_{th}$ described herein that accounts for both Mode I and Mode II load forces may be obtained by conducting a series of standardized asymmetric four-point bending (AFPB) tests on a test specimen having substantially the same composition (e.g., the same or nearly the same composition) as the machine component being analyzed. Descriptions of a AFPB tests may be found "Asymmetric Four-Point Crack Specimen," by He, M. Y. and Hutchinson, J. W., Journal of Applied Mechanics, Volume 67, March 2000, pg. 207-209, the contents of which is hereby incorporated by reference in its entirety. FIG. 1 shows a conceptual side view of an example standardized AFPB apparatus 10, which includes controller 36, test specimen 12 having initial notch 32, inner load bars 14, outer load bars 16, and force plates 18. Test specimen 12 may be placed in AFPB apparatus 10 such that inner loading bars 14 and outer loading bars 16 contact test specimen 12 along set positions, with each load plate of load plates 18 contacting one of the inner loading bars 14 and one of the outer loading bars 16 such that load plates 18 are on opposite sides of test specimen 12. During testing, controller 36 controls a force generating apparatus, such as a hydraulic or mechanical press to apply cyclic load force 34 across load plates 18, which transfers cyclic load force 34 along load axis 30 to test specimen 12 via the inner and outer loading rods 14 and 16.

Inner load bars 14 may be offset from load axis 30 by a set distance $M_I$ (e.g., 10 mm) and outer load bars 16 may be offset from load axis 30 by a set distance $M_O$ (e.g., two times $M_I$ or 20 mm). In some examples, inner and outer loading rods 14 and 16 may be coated with a lubricant to reduce frictional forces between the loading rods and test specimen 12.

Test specimen 12 may define a length (L) of at least $2M_O$, e.g., greater than 40 mm, a thickness (w) of about 4 mm, and include initial notch 32. Initial notch 32 may be characterized by notch length c (e.g., about 2.2 mm) extending substantially perpendicular (e.g., perpendicular or nearly perpendicular) from the surface of test specimen 12. Initial notch 32 may be initially created using any suitable means including, for example, using electro-discharge machining (EDM). Once created, initial notch 32 acts as a simulated flaw from which a fatigue crack can propagate from during the cyclic load experiments. As the fatigue crack grows, notch length c will increase (e.g., the length of initial notch 32 plus the length of fatigue crack growth).

During testing, controller 36 may control the force generating apparatus to apply cyclic load force 34 to load plates 18. In some examples, cyclic load force 34 may be characterized by a cyclic load frequency (e.g., about 10 Hz) resonating between a maximum exerted stress intensity factor $K_{max}$ and a minimum exerted stress intensity factor $K_{min}$ with a set load ratio R defined by Equation 2. In some examples the load ratio, R, may be selected based on the anticipated stress cycle to be applied to the machine component 20, which may be defined by $\sigma_{max}$ and $\sigma_{min}$. In some examples, the load ratio R may be between about 0.05 and about 0.8.

$$R = K_{min}/K_{max} = \sigma_{min}/\sigma_{min} \quad \text{(Equation 2)}$$

The change between the maximum exerted stress intensity factor $K_{max}$ and the minimum exerted stress intensity factor $K_{min}$ define the applied stress intensity factor $\Delta K$ exerted on test specimen 12 as shown by Equation 3.

$$\Delta K = K_{max} - K_{min} \quad \text{(Equation 3)}$$

Figure 6:
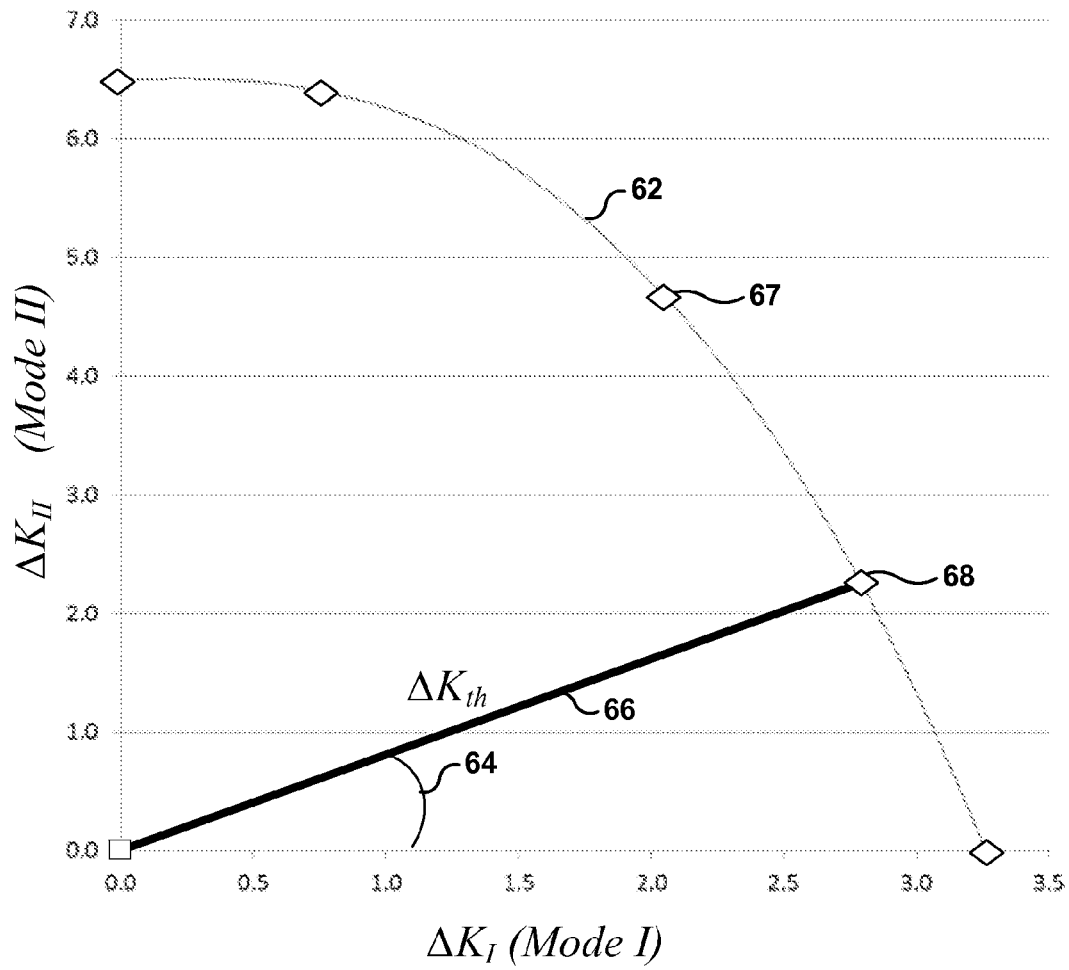
FIG. 6 is a graphical representation of an example mixed-mode dataset of standardized asymmetric four-point bending test that plots the threshold Mode I against the threshold Mode II stress intensity factors

The stress intensity factor $\Delta K$ may be further characterized by a Mode I and a Mode II component (e.g., $\Delta K_I$ and $\Delta K_{II}$ respectively), which may be determined by Equations 4 and 5 respectively.

$$\Delta K_I = \Delta \sigma_I \sqrt{\pi S} \beta \quad \text{(Equation 4)}$$

$$\Delta K_{II} = \Delta \sigma_{II} \sqrt{\pi S} \beta \quad \text{(Equation 5)}$$

where $\Delta K_I$ is the Mode I stress intensity factor, $\Delta K_{II}$ is the Mode II stress intensity factor, $\Delta \sigma_I$ is the Mode I change in stress ($\sigma_{max} - \sigma_{min}$) for a single stress cycle, $\Delta \sigma_{II}$ is the mode II change in stress for a stress single cycle, S is the offset length between the positioning of initial notch 32 relative to load axis 30 (see FIG. 1), and $\beta$ is the geometry correction factor from Equation 1. The degree of mixed-mode load forces (e.g., Mode I and Mode II) exerted on test specimen 12 depends on the positioning of initial notch 32 relative to load axis 30 (e.g., distance S). Equations 6 and 7 provide an example equation of determining the degree of mixed-mode load forces applied to test specimen 12 based on the distance S.

$$\Delta K_I = \sqrt{\pi c}\left(\frac{6S\Delta Q}{w^2}\right) \quad \text{(Equation 6)}$$

$$\left(\sqrt{\frac{(2w)\tan(\pi c/2w)}{\pi c}}\left(\frac{0.923 + 0.199\left(1 - \sin\frac{\pi c}{2w}\right)^4}{\cos\left(\frac{\pi c}{2w}\right)}\right)\right)$$

$$\Delta K_{II} = \quad \text{(Equation 7)}$$

$$\left(\frac{\Delta Q}{w^{0.5}}\right)\frac{(c/w)^{1.5}}{(1-c/w)^{0.5}}\left[7.264 - 9.37\left(\frac{c}{w}\right) + 2.74\left(\frac{c}{w}\right)^2 + 1.87\right.$$

$$\left.\left(\frac{c}{w}\right)^3 - 1.04\left(\frac{c}{w}\right)^4\right]$$

$$\text{for } 0 \leq \frac{c}{w} \leq 1$$

where S is the offset length between the positioning of initial notch 32 relative to load axis 30 (see FIG. 1), c is the length of initial notch 32 and any subsequent growth propagation from initial notch 32, w is the thickness of test specimen 12, $\Delta Q$ is the shear force determined according to Equation 8 below.

$$\Delta Q = \Delta P\left(\frac{M_o - M_I}{M_o + M_I}\right) \quad \text{(Equation 8)}$$

where $\Delta P$ is the cyclic load force 34 applied to test sample 12. As can be seen from the above equations, the Mode II load force is independent of length S while the Mode I load force depends on length S. Thus, for a pure Mode II load force, initial notch 32 may be positioned such that S=0. The ratio of Mode I and Mode II stress intensity factors may be characterized by a phase angle γ in accordance with Equation 8.

$$\gamma = \tan^{-1}\left[\frac{\Delta K_{II}}{\Delta K_I}\right] \quad \text{(Equation 8)}$$

where phase angle γ defines the degree of Mode I and Mode II stress intensity factors $\Delta K_I$ and $\Delta K_{II}$ as shown in FIG. 6.

In some examples, to obtain a threshold stress intensity factor (e.g., $\Delta K_{th}$) for a given phase angle γ, controller 36 may control the force generating apparatus to incrementally increase cyclic load force 34 applied to test specimen 12 until significant growth of a fatigue crack from initial notch 32 occurs. For example, controller 36 may apply an initial cyclic load force 34 to test specimen 12 for a set number of cycles (e.g., about 50,000 cycles) followed by the examination of initial notch 32 for the presence of a fatigue crack using any number of inspection techniques including, for example, ultrasonic testing, visual/microscopic inspection, scanning electron microscopy, eddy current or the like, to determine if the length c of initial notch 32 and/or the propagation of a fatigue crack therefrom has significantly increased (e.g., growth by more than 2%). If the length c of initial notch 32 has not significantly increased, controller 36 may incrementally increase cyclic load force 34 (e.g., increased by 4%) and controller 36 may reapply cyclic load force 34 to test specimen 32 for an additional set number of cycles while maintaining the load ratio R (Equation 2) and the phase angle γ (Equation 8).

Once the fatigue crack that originates from initial notch 32 undergoes significant growth (e.g., growth by more than 2%), controller 36 may record the testing conditions and, using the above equations, formulate a dataset including the threshold stress intensity factor $\Delta K_{th}$ corresponding to the point of significant growth of initial notch 32, the threshold stress intensity factors for Mode I and Mode II load forces (e.g., $\Delta K_I$ and $\Delta K_{II}$ respectively), and the associated phase angle γ.

The AFPB test may be repeated on a new test specimen 12, to examine a different phase angle γ using a similar technique, and the results may be added to the corresponding dataset. In some examples, the dataset may be formed and stored by controller 36 on a computer-readable storage medium and accessed via a computer processor. Computer-readable storage media may include random access memory (RAM), read only memory (ROM), programmable read only memory (PROM), erasable programmable read only memory (EPROM), electronically erasable programmable read only memory (EEPROM), flash memory, a hard disk, a compact disc ROM (CD-ROM), a floppy disk, a cassette, magnetic media, optical media, or other computer system readable media.

Figure 2:
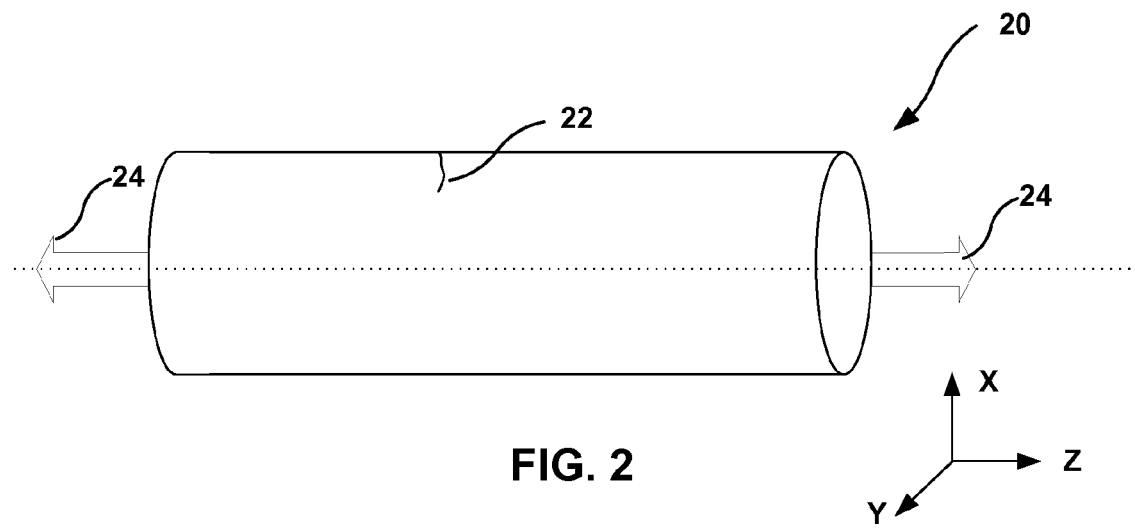
FIG. 2 is a conceptual perspective view of an example machine component including a fatigue crack.
Figure 3:
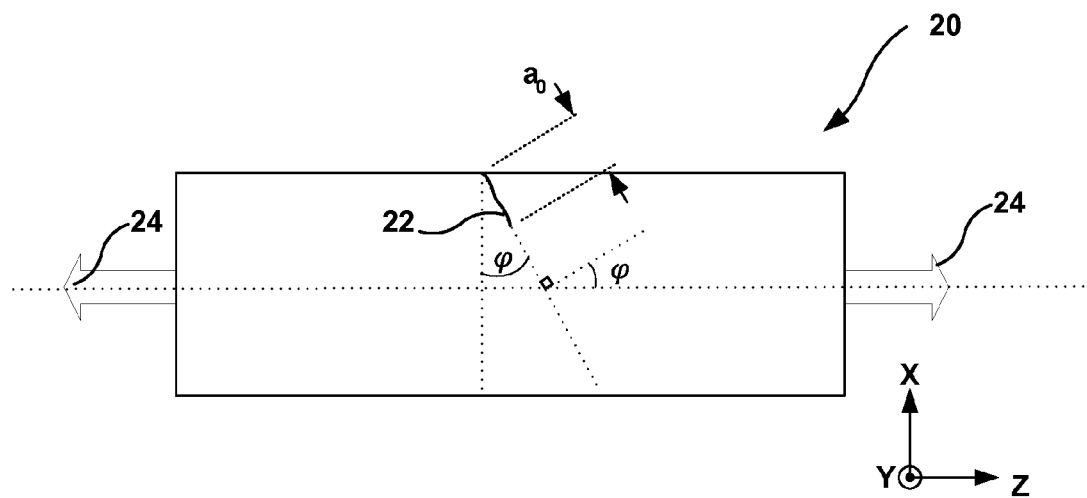
FIG. 3 is a conceptual cross-sectional view of an example machine component including a fatigue crack.

To determine the threshold stress intensity factor (e.g., $\Delta K_{th}$) of a particular machine component, the phase angle γ may be selected to correspond to the observed fatigue crack angle φ of a fatigue crack in the machine component. For example, FIGS. 2 and 3 shows conceptual perspective and cross-sectional views respectively of an example machine component 20 including a fatigue crack 22 subjected to anticipated loads 24. Machine component 20 includes fatigue crack 22 having an initial fatigue crack length $a_o$ originating from the surface of machine component 20. Fatigue crack 22, may extend from the surface of machine component 20 towards the center of the component at a fatigue crack angle φ as measured between the linear direction of fatigue crack 22 (e.g., the direction in which fatigue crack 22 may propagate) and the orthogonal to the direction of the anticipated loads 24 (e.g., perpendicular to the load force direction). The fatigue crack angle, may also be measured as the angle between the normal to the plane defined by fatigue crack 22 and the principle stress direction (e.g., the direction of anticipated loads 24). In some examples, machine component 20 may be in the form of a shaft, gas turbine engine disks and spacers or other component that experiences tensile loading (e.g., Mode I), shear (e.g., Mode II), and/or other load forces. Machine component 20 may include, for example, engine components (e.g., turbine engine disks or spacers, crankshafts, connecting rods, valves, retaining bolts, or the like), structural components (e.g., chassis, frames, tie rods, drive shafts, or the like), manufacturing components, or the like.

Fatigue crack length $a_o$ and fatigue crack angle φ may be detected and measured through any number of inspection techniques discussed above including, for example, ultrasonic testing, visual/microscopic inspection, scanning electron microscopy, eddy current or the like. In some examples, the fatigue crack angle φ may be zero degrees (e.g., fatigue crack 22 lies substantially perpendicular, e.g., perpendicular or nearly perpendicular, to anticipated loads 24) resulting in mostly Mode I load forces exerted on fatigue crack 22. In other examples, the fatigue crack angle φ may approach ninety degrees (e.g., fatigue crack 22 lies substantially parallel, e.g., parallel or nearly parallel, to anticipated loads 24) resulting in mostly Mode II load forces exerted on fatigue crack 22.

Based on the observed fatigue crack angle φ of fatigue crack 22 and the anticipated stress cycle A based on loads 24, the threshold stress intensity factor (e.g., $\Delta K_{th}$) for machine component 20 may be determined by selecting a phase angle γ that corresponds to the fatigue crack angle φ to determine the corresponding threshold stress intensity factor (e.g., $\Delta K_{th}$) for the selected phase angle γ. For example, controller 36 may be configured to apply a regression analysis (e.g., linear or non-linear) to the dataset obtained from the AFPB experiments to determine the threshold stress intensity factor (e.g., $\Delta K_{th}$) as a function of phase angle γ. Controller 36 may then select a phase angle γ that corresponds to the fatigue crack angle φ of fatigue crack 22 and preform the regression analysis to calculate the corresponding threshold stress intensity factor (e.g., $\Delta K_{th}$) for the selected phase angle γ.

In such configurations, the evaluation of the dataset by controller 36 may be implemented, at least in part, in hardware, software, firmware, or any combination thereof. The various aspects of the described evaluation may be implemented within one or more processors, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. Controller 36 including hardware may also perform one or more of the techniques of this disclosure.

Additionally or alternatively, controller 36 may be configured to determine threshold stress intensity factor (e.g., $\Delta K_{th}$) graphically by plotting the dataset obtained from the AFPB experiments. For example, FIG. 6 shows a graphical representation of an example mixed-mode dataset 67 of standardized AFPB test that plots the threshold Mode I against the threshold Mode II stress intensity factors (e.g., $\Delta K_I$ and $\Delta K_{II}$ respectively). Controller 36 may perform a regression analysis on dataset 67 to fit a curve (e.g., fitted curve 62) to the plotted dataset 67. Fitted curve 62 represents the threshold point where significant fracture growth is obtained depending on the proportion of mixed-mode load forces applied to test specimen 12 (e.g., the threshold point dependent on phase angle γ). For a given phase angle γ, the threshold stress intensity factor (e.g., $\Delta K_{th}$) is represented by the magnitude of a line that extends from the origin and intersects with fitted curve 62 (e.g., line 66), where the phase angle γ (e.g., angle 64) corresponds to the angular displacement between the x-axis and the intersecting line (e.g., line 66). For a specific fatigue crack angle φ, controller 36 may determine the corresponding threshold stress intensity factor (e.g., $\Delta K_{th}$) by adjusting line 66 such that phase angle 64 corresponds to fatigue crack angle φ and determining the magnitude of line 66 at the point of intersection 68 with fitted curve 62.

Additionally or alternatively, in some examples mixed-mode dataset 67 may be configured to plot the threshold stress intensity factor (e.g., $\Delta K_{th}$) as a function of the phase angle γ to provide a direct relationship between the threshold stress intensity factor (e.g., $\Delta K_{th}$) and the phase angle γ. In such examples, a corresponding threshold stress intensity factor (e.g., $\Delta K_{th}$) for a specific fatigue crack angle φ, may be directly observed from the plotted dataset 67.

Figure 7:
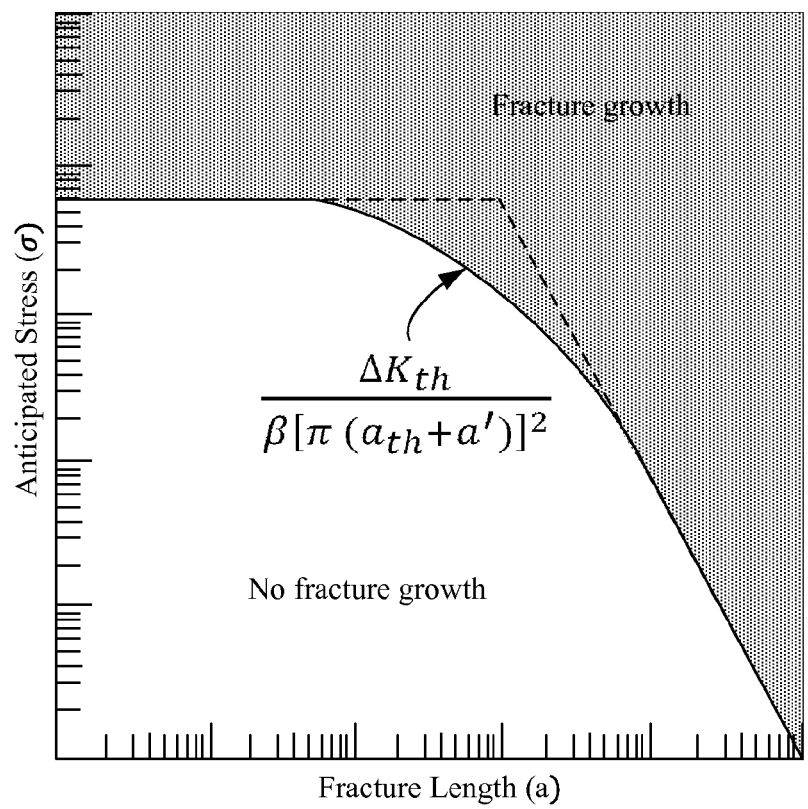
FIG. 7 is a logarithmic graphical representation of Equation 1.

Based on the threshold stress intensity factor $\Delta K_{th}$ determined for the fatigue crack angle cp, Controller 36 may then determine a corresponding threshold crack lengths $a_{th}$ for fatigue crack 22 using Equation 1. Additionally or alternatively, controller 36 may represent Equation 1 graphically. For example FIG. 7 is a logarithmic graphical representation of Equation 1 plotting the log of the fatigue crack length a versus the log of the anticipated stress σ (e.g., fatigue crack length $a_o$ and anticipated loads 24 of machine component 20). As shown, the white region represents the parameters where no substantial growth of fatigue crack 22 is observed (e.g., fatigue crack length $a_o$ below the threshold crack length $a_{th}$), the grey region represents the parameters where substantial growth of fatigue crack 22 is expected (e.g., fatigue crack length $a_o$ greater than the threshold crack length $a_{th}$), and the boundary between the two regions is characterized by Equation 1.

In some examples, the determined threshold crack length $a_{th}$ may be used for quality control purposes. For example, if the measured fatigue crack length $a_o$ of machine component 20 is greater than or equal to the determined threshold crack length $a_{th}$, machine component 20 may be categorized as unsatisfactory for the particular application and discarded or classified for acceptable for particular applications (e.g., applications where the anticipated loads 24 sufficiently low such that the resultant threshold crack length $a_{th}$ is greater than the measured fatigue crack length $a_o$).

While analysis of the dataset obtained from the AFPB experiments is described above as being conducted by controller 36, such analysis may be conducted using a variety of techniques. For example, in some examples the analysis of the dataset may be performed by a user without the aid controller 36. In other examples, the analysis of the dataset may be performed by a user with the aid of one or more additional or alternative processors.

Figure 8:
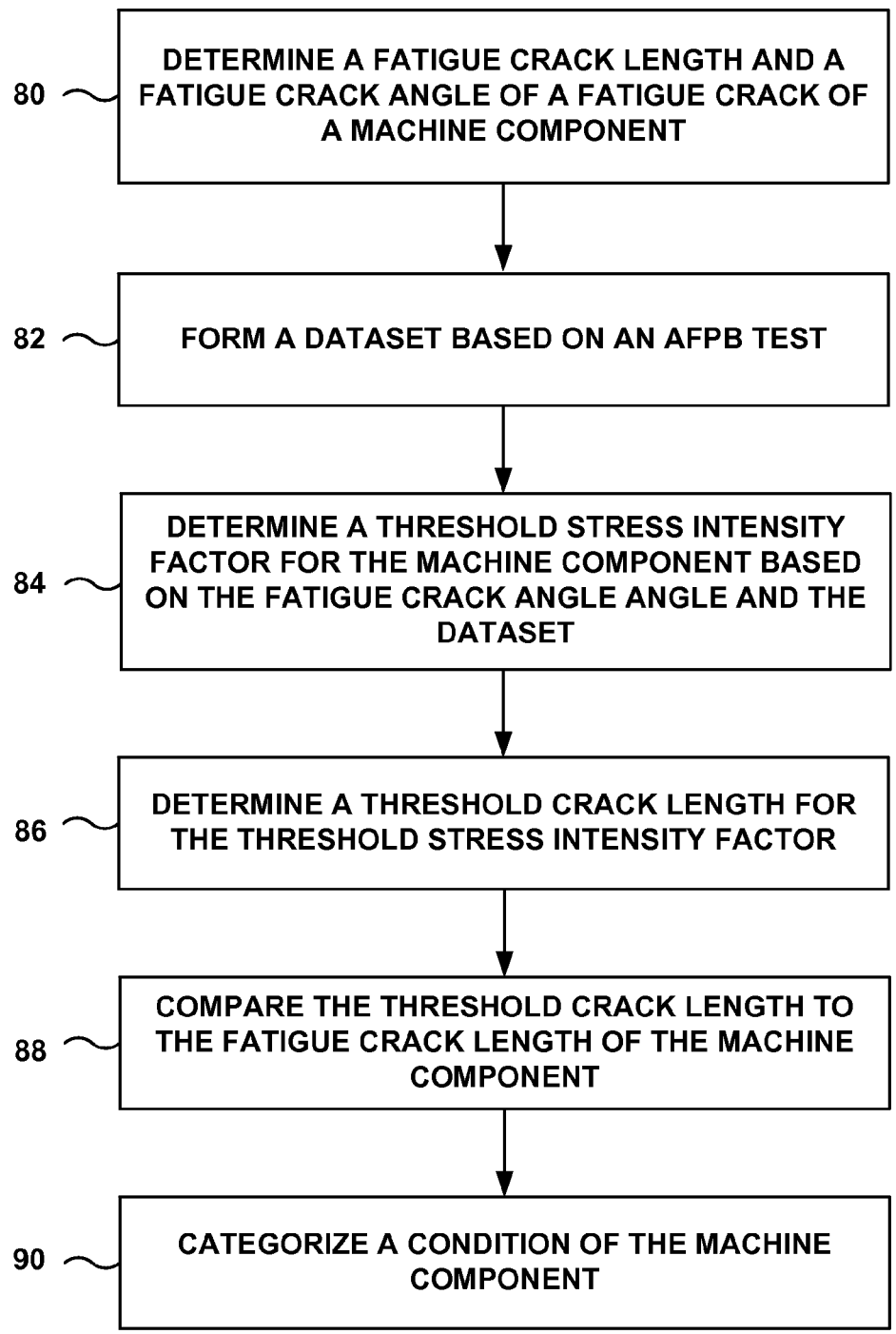
FIG. 8 is a flow diagram illustrating example techniques for determining a threshold crack length for a measured fatigue crack.

FIG. 8 is a flow diagram illustrating example techniques for determining a threshold crack length for a measured fatigue crack. FIG. 8 is described below in reference to FIGS. 1-3 for illustrative purposes, however, such descriptions are not intended to be limiting.

FIG. 8 illustrates an example technique that includes determining a fatigue crack length $a_o$ and a fatigue crack angle φ of a fatigue crack 22 of a machine component 20 (80). As described above, fatigue crack 22 may be characterized using any one or more of a variety of techniques, including, for example, ultrasonic testing, visual/microscopic inspection, scanning electron microscopy, eddy current or the like.

The technique of FIG. 8 also includes forming a dataset based on conducting an AFPB test (82). As described above, using AFPB apparatus 10, controller 36 may perform a series of AFPB tests on test specimens, e.g., test specimens 12, having a composition substantially similar to that of machine component 20. Controller 36 may perform the AFPB tests for a variety of mixed-mode phase angles γ to develop a representative dataset of corresponding threshold stress intensity factors (e.g., $\Delta K_{th}$) (82). In some examples, the dataset may be formed (82) and stored on a computer-readable storage medium and accessed via controller 36.

As described above, using the fatigue crack angle φ of fatigue crack 22, controller 36 may determine a threshold stress intensity factor $\Delta K_{th}$ for the machine component 20 (84) by determining the threshold stress intensity factor $\Delta K_{th}$ for a mixed-mode phase angles γ that corresponds to the fatigue crack angle φ of machine component 20. In some examples, controller 36 may present the dataset in graphical format, for example, as described above with respect to FIG. 6 and determine the threshold stress intensity factor (e.g., $\Delta K_{th}$) (84) based on the plotted dataset 67.

The technique of FIG. 8 also includes determining the threshold crack length $a_{th}$ for machine component 20 based on the derived threshold stress intensity factor $\Delta K_{th}$ (88). Controller 36 may determine a threshold crack length $a_{th}$ using Equation 1 as described above (88). Next the resultant threshold crack length $a_{th}$ may be compared to the fatigue crack length $a_o$ of fatigue crack 22 (88) to categorize a condition of machine component 20 (90). Such categorizations (90) may include, for example, marking machine component 20 as unsatisfactory or a factory-second if the fatigue crack length $a_o$ of machine component 20 is greater than or equal to the threshold crack length $a_{th}$. Additionally or alternatively, the machine component 20 may be categorized (90) as satisfactory and subsequently installed in a device if the fatigue crack length $a_o$ of machine component 20 is less than the threshold crack length $a_{th}$.

Various examples have been described. These and other examples are within the scope of the following claims.

What is claimed is:

1. A method comprising:
   determining a fatigue crack length and a fatigue crack angle of a fatigue crack of a machine component, wherein the fatigue crack angle is measured as an angle between a normal to a plane defined by the fatigue crack and a direction of the anticipated cyclic load force to be applied to the machine component;
   determining a component threshold stress intensity factor for the fatigue crack, wherein the component threshold stress intensity factor is determined from a dataset formed by at least conducting an asymmetric four point bend test on a test specimen having an initial notch, wherein the dataset includes at least one respective threshold stress intensity factor and at least one mixed-mode phase angle, wherein each respective threshold stress intensity factor of the at least one respective threshold stress intensity factor is associated with a corresponding mixed-mode phase angle of the at least one mixed-mode phase angle, and wherein the component threshold stress intensity factor is based at least in part on a threshold stress intensity factor associated with a mixed-mode phase angle that corresponds to the fatigue crack angle;

determining a threshold crack length for the component threshold stress intensity factor based on the following equation:

$$a_{th} = \frac{1}{\pi}\left[\frac{\Delta K_{th}}{\Delta \sigma \beta}\right]^2 - a'$$

where $a_{th}$ is the threshold crack length, $\Delta K_{th}$ is the component threshold stress intensity factor, $\Delta\sigma$ is the anticipated stress cycle to be applied to the machine component, $\beta$ is a geometry correction factor, and $a'$ is a small-crack correction factor; and categorizing a condition of the machine component based at least in part on a comparison between the threshold crack length and the fatigue crack length of the fatigue crack in the machine component.

2. The method of claim 1, further comprising:
forming the dataset by at least:
conducting a plurality of asymmetric four point bend tests, wherein each asymmetric four point bend test is conducted at a respective mixed-mode phase angle on a respective test specimen having a respective initial notch to determine a respective threshold stress intensity factor that results in a growth of a crack from the initial notch, wherein each respective test specimen has a composition substantially similar to the machine component; and
associating the respective threshold stress intensity factor with the respective mixed-mode phase angle.

3. The method of claim 2, further comprising:
plotting the dataset to represent the threshold stress intensity factor as a function of the mixed-mode phase angle.

4. The method of claim 1, wherein categorizing the condition of the machine component comprises identifying the machine component as unsatisfactory in response to the fatigue crack length of the machine component being greater than or equal to the threshold crack length.

5. The method of claim 1, wherein categorizing the condition of the machine component comprises identifying the machine component as satisfactory and installing the machine component in a device in response to the fatigue crack length of the machine component being less than the threshold crack length.

6. The method of claim 1, wherein the dataset is stored on a computer-readable storage medium, and wherein determining a component threshold stress intensity factor for the fatigue crack angle is conducted using a programmable processor configured to determine the component threshold stress intensity factor based on the fatigue crack angle using the dataset.

7. The method of claim 1, wherein $\beta$ is set at 1, and $a'$ is set at zero.

8. A method comprising:
determining a fatigue crack length and a fatigue crack angle of a fatigue crack of a machine component, wherein the fatigue crack angle is measured as an angle between a normal to a plane defined by the fatigue crack and a direction of the anticipated cyclic load force to be applied to the machine component;

conducting an asymmetric four point bend test at a mixed-mode phase angle on a test specimen having an initial notch to determine a threshold stress intensity factor that results in a growth of a crack from the initial notch, wherein the mixed-mode phase angle is set to equal the fatigue crack angle of the machine component, wherein the test specimen has a composition substantially similar to the machine component;

determining a threshold crack length for the threshold stress intensity factor based on the following equation:

$$a_{th} = \frac{1}{\pi}\left[\frac{\Delta K_{th}}{\Delta \sigma \beta}\right]^2 - a'$$

where $a_{th}$ is the threshold crack length, $\Delta K_{th}$ is the component threshold stress intensity factor, $\Delta\sigma$ is the anticipated stress cycle to be applied to the machine component, $\beta$ is a geometry correction factor, and $a'$ is a small-crack correction factor;

comparing the threshold crack length to the fatigue crack length of the fatigue crack of the machine component; and categorizing a condition of the machine component based on the comparing the threshold crack length to the fatigue crack length of the fatigue crack in the machine component.

9. The method of claim 8, wherein categorizing a condition of the machine component includes identifying the machine component as unsatisfactory if the fatigue crack length of the machine component is greater than or equal to the threshold crack length.

10. The method of claim 8, wherein categorizing a condition of the machine component includes identifying the machine component as satisfactory and installing the machine component in a device if the fatigue crack length of the machine component is less than the threshold crack length.

11. The method of claim 8, wherein $\beta$ is set at 1, and $a'$ is set at zero.

12. A device comprising:
A processor configured to analyze a dataset to determine a component threshold stress intensity factor for a machine component, wherein the machine component includes a fatigue crack having a fatigue crack length and a fatigue crack angle measured as an angle between a normal to a plane defined by the fatigue crack and a direction of the anticipated cyclic load force to be applied to the machine component, wherein the dataset is formed by at least conducting an asymmetric four point bend test on a test specimen having an initial notch, wherein the dataset includes at least one respective threshold stress intensity factor and at least one mixed-mode phase angle, wherein each respective threshold stress intensity factor of the at least one respective threshold stress intensity factor is associated with a corresponding mixed-mode phase angle of the at least one mixed-mode phase angle, and wherein the component threshold stress intensity factor is based at least in part on a threshold stress intensity factor associated with a mixed-mode phase angle that corresponds to the fatigue crack angle, wherein the processor is configured to determine a threshold crack length for the machine component using the component threshold stress intensity factor based on the following equation:

$$a_{th} = \frac{1}{\pi}\left[\frac{\Delta K_{th}}{\Delta\sigma\beta}\right]^2 - a'$$

where $a_{th}$ is the threshold crack length, $\Delta K_{th}$ is the component threshold stress intensity factor, $\Delta\sigma$ is the anticipated stress cycle to be applied to the machine component, $\beta$ is a geometry correction factor, and $a'$ is a small-crack correction factor, and wherein the processor is configured to compare the threshold crack length and the fatigue crack length and categorize a condition of the machine component based at least in part on the comparison.

13. The device of claim 12, further comprising a computer-readable storage medium comprising the dataset and instructions for causing the processor to analyze the dataset to determine the component threshold stress intensity factor and the threshold crack length for the machine component.

14. The device of claim 12, wherein $\beta$ is set at 1, and $a'$ is set at zero.

\* \* \* \* \*